(12) United States Patent
Kullas et al.

(10) Patent No.: US 10,524,896 B2
(45) Date of Patent: Jan. 7, 2020

(54) IMPLANTABLE PROSTHESIS FOR RECONSTRUCTION OF AN ANATOMICAL FEATURE

(75) Inventors: Karen E. Kullas, Berkley, MA (US); Tami L. Rathbun, Exeter, RI (US)

(73) Assignee: C.R. Bard, Inc., Murray Hill, NJ (US)

( * ) Notice: Subject to any disclaimer, the term of this patent is extended or adjusted under 35 U.S.C. 154(b) by 1268 days.

(21) Appl. No.: 14/131,661

(22) PCT Filed: Jul. 8, 2011

(86) PCT No.: PCT/US2011/043332
§ 371 (c)(1),
(2), (4) Date: Jun. 23, 2014

(87) PCT Pub. No.: WO2013/009282
PCT Pub. Date: Jan. 17, 2013

(65) Prior Publication Data
US 2014/0309737 A1    Oct. 16, 2014

(51) Int. Cl.
*A61F 2/12* (2006.01)
*A61F 2/00* (2006.01)

(52) U.S. Cl.
CPC ........ *A61F 2/12* (2013.01); *A61F 2002/0086* (2013.01); *A61F 2220/0075* (2013.01);
(Continued)

(58) Field of Classification Search
CPC ................. A61F 2/12; A61F 2002/526; A61F 2002/4475; A61F 2220/0025;
(Continued)

(56) References Cited

U.S. PATENT DOCUMENTS

| 4,778,465 A | 10/1988 | Wilkins |
| 4,790,309 A | 12/1988 | Becker |

(Continued)

FOREIGN PATENT DOCUMENTS

| CA | 2342480 A1 * | 9/2002 | ............... A61F 2/52 |
| WO | WO 96/29043 A1 | 9/1996 | |

(Continued)

OTHER PUBLICATIONS

Extended European Search Report for European Patent Application No. 11869462.9, dated Nov. 26, 2014 (4 pages).

(Continued)

*Primary Examiner* — Brian E Pellegrino
(74) *Attorney, Agent, or Firm* — Wolf, Greenfield & Sacks, P.C.

(57) ABSTRACT

An implantable prosthesis is provided for reconstructing an anatomical feature, such as a breast nipple. The prosthesis may be formed from a biologic and/or synthetic material. The prosthesis may include a body with a shape that is suitable for reconstructing the anatomical feature. A base may be located at an end of the body to facilitate anchoring the prosthesis in position. The prosthesis may be provided with openings that allow fluid flow therethrough, tissue ingrowth, revascularization, neovascularization and/or fat or stem cell deposition. The prosthesis may include a plurality of layers of biocompatible material arranged in a stacked configuration. The layers may be in spaced relation relative to each other and secured or fixed in position to maintain the spacing therebetween. Each layer may have one or more openings extending therethrough. The spaced layer arrangement may provide a desired tactile response and/or natural movement for the prosthesis.

32 Claims, 8 Drawing Sheets

(52) U.S. Cl.
CPC . *A61F 2230/0091* (2013.01); *A61F 2250/006* (2013.01); *A61F 2250/0051* (2013.01)

(58) Field of Classification Search
CPC ..... A61F 2002/4415; A61F 2220/0075; A61B 90/39; A61B 90/02
See application file for complete search history.

(56) References Cited

U.S. PATENT DOCUMENTS

| | | | |
|---|---|---|---|
| 5,116,370 A * | 5/1992 | Foglietti | A61F 2/12 623/8 |
| 5,171,321 A | 12/1992 | Davis | |
| 5,300,120 A * | 4/1994 | Knapp | A01K 11/006 623/11.11 |
| 5,301,692 A | 4/1994 | Knowlton | |
| 5,306,310 A * | 4/1994 | Siebels | A61F 2/44 623/17.13 |
| 5,356,429 A * | 10/1994 | Seare | A61F 2/12 623/8 |
| 5,836,912 A | 11/1998 | Kusleika | |
| 5,882,353 A * | 3/1999 | VanBeek | A61B 90/02 623/8 |
| 6,071,309 A | 6/2000 | Knowlton | |
| 6,099,566 A * | 8/2000 | Vonderharr | A61F 2/12 623/8 |
| 6,497,609 B1 | 12/2002 | Cobbs | |
| 7,566,344 B2 | 7/2009 | Hansen | |
| 2001/0005784 A1 | 6/2001 | Righetti | |
| 2004/0143325 A1 | 7/2004 | Holmes | |
| 2004/0143326 A1 | 7/2004 | Holmes | |
| 2005/0059864 A1* | 3/2005 | Fromovich | A61B 90/02 600/201 |
| 2006/0265077 A1* | 11/2006 | Zwirkoski | A61B 17/7094 623/17.16 |
| 2007/0088445 A1 | 4/2007 | Patel et al. | |
| 2008/0071370 A1 | 3/2008 | Vinas | |
| 2008/0208358 A1 | 8/2008 | Bellamkonda et al. | |
| 2009/0118836 A1* | 5/2009 | Cordaro | A61F 2/4455 623/17.16 |
| 2010/0137999 A1 | 6/2010 | Shohat | |
| 2010/0228184 A1 | 9/2010 | Mavani et al. | |
| 2010/0241162 A1 | 9/2010 | Obermiller et al. | |
| 2010/0249828 A1 | 9/2010 | Mavani et al. | |
| 2010/0249830 A1 | 9/2010 | Nelson | |
| 2010/0331612 A1 | 12/2010 | Lashinski et al. | |
| 2012/0101575 A1* | 4/2012 | Horne | A61F 2/12 623/8 |
| 2013/0211519 A1* | 8/2013 | Dempsey | A61F 2/12 623/8 |
| 2014/0303603 A1 | 10/2014 | Kullas et al. | |

FOREIGN PATENT DOCUMENTS

| | | |
|---|---|---|
| WO | WO 02/22047 A1 | 3/2002 |
| WO | WO 2004/066888 A1 | 8/2004 |
| WO | WO 2007/075411 A2 | 7/2007 |
| WO | WO 2007/084285 A2 | 7/2007 |
| WO | WO 2007/149989 A2 | 12/2007 |
| WO | WO 2009/070686 A1 | 6/2009 |
| WO | WO 2010/019292 A1 | 2/2010 |
| WO | WO 2010/028300 A1 | 3/2010 |

OTHER PUBLICATIONS

Extended European Search Report for EP16152980.5 dated May 9, 2016 (4 pages).
International Search Report and Written Opinion of the International Searching Authority for International application No. PCT/US11/43320, dated Nov. 16, 2011 (11 pages).
International Search Report and Written Opinion of the International Searching Authority for International application No. PCT/US11/43332, dated Nov. 15, 2011 (11 pages).
Extended European Search Report for EP17168334.5, dated Jul. 21, 2017, 7 pages.
U.S. Appl. No. 14/131,641, filed Jun. 23, 2014, Kullas et al.

* cited by examiner

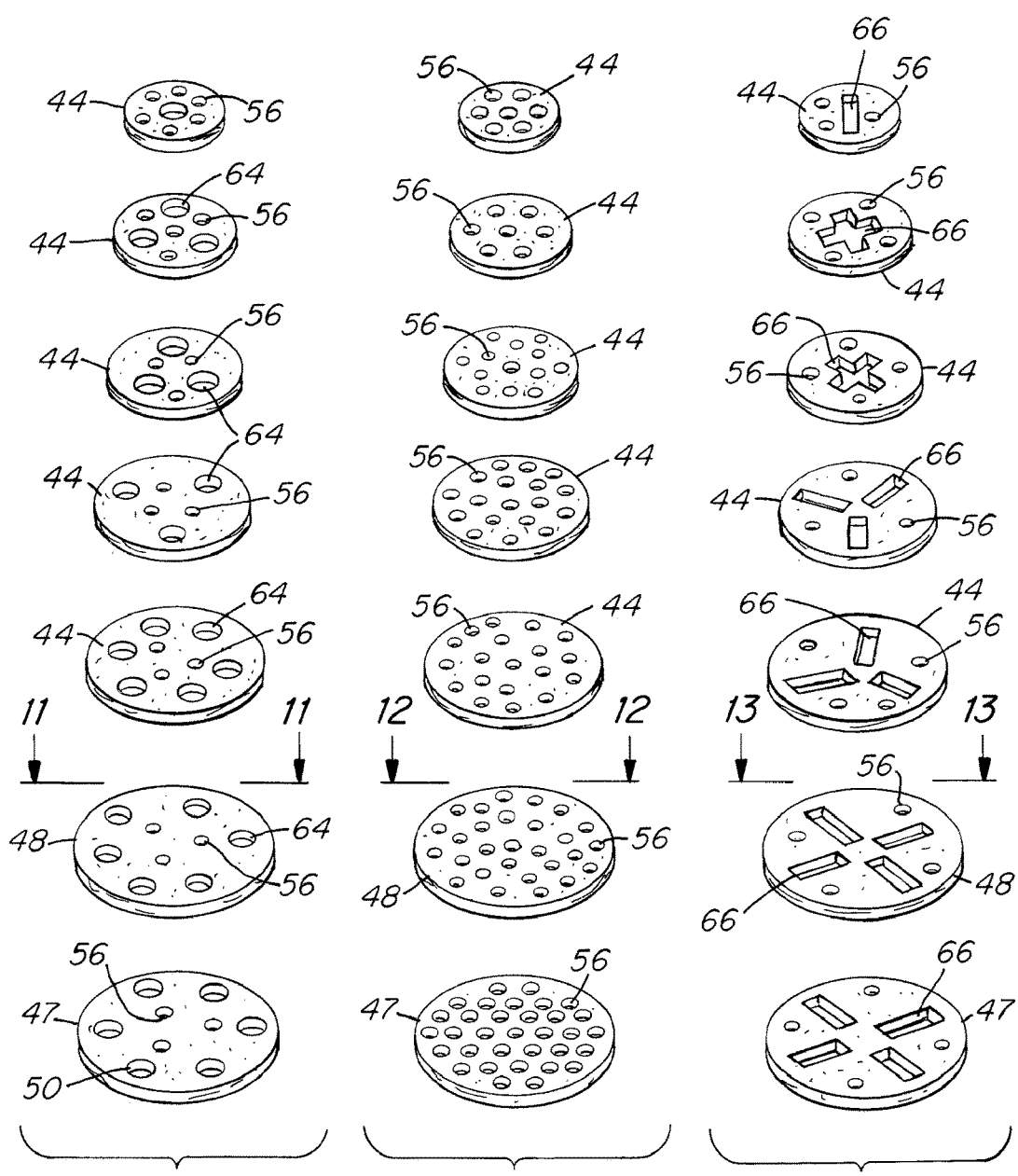
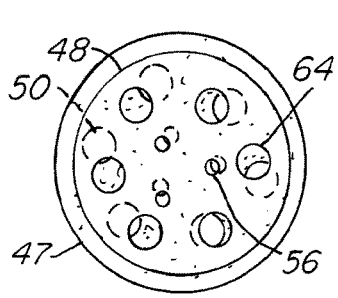
Fig. 11
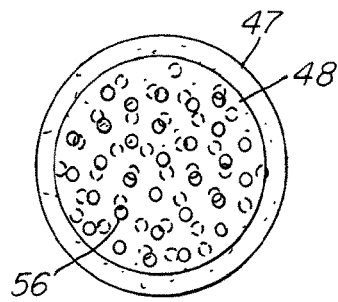
Fig. 12
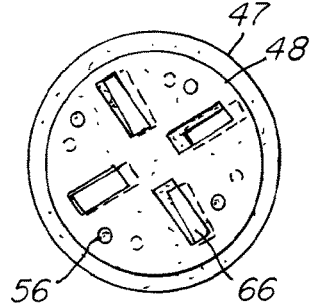
Fig. 13

IMPLANTABLE PROSTHESIS FOR RECONSTRUCTION OF AN ANATOMICAL FEATURE

RELATED CASE INFORMATION

This application is a 371 U.S. National Stage of International Application No. PCT/US2011/043332, filed on Jul. 8, 2011, which is incorporated by reference herein in its entirety.

FIELD

The present invention relates to an implantable prosthesis, and more particularly to an implantable prosthesis for reconstruction of an anatomical feature, such as a breast nipple.

BACKGROUND

A mastectomy may involve removal of all or part of a patient's breast tissue and nipple. Following a mastectomy, the patient may undergo a breast reconstruction procedure that involves placing a breast implant under the pectoralis major muscle to provide the patient with the look and feel of a natural breast. Breast reconstruction may also involve the reconstruction or replacement of a breast nipple.

It has been proposed to reconstruct or replace a nipple by implanting a rolled piece of a biologic material. The prosthesis may resemble a cylinder that is sutured in place.

It has also been proposed to reconstruct or replace a nipple by implanting a tube-like cylinder of material that does not overlap itself.

SUMMARY

The present invention relates to an implantable prosthesis and a method of reconstructing an anatomical feature. The method and prosthesis may have particular application for reconstructing a breast nipple.

In one embodiment, an implantable prosthetic nipple comprises a body formed of implantable biocompatible material and having a shape to reconstruct a breast nipple. The prosthetic nipple also comprises a base formed of implantable biocompatible material that is located at a first end of the body. The base has a dimension that is larger than the body. Each of the body and the base has at least one opening extending therethrough.

In another embodiment, an implantable prosthetic nipple comprises a base formed of an implantable biocompatible material having a shape to reconstruct a breast areola, and a nipple body formed of an implantable biocompatible material supported by the base. The body includes a plurality of disks that are arranged in a stacked configuration with each disk being positioned in spaced relation to an adjacent disk.

In a further embodiment, a method of reconstructing a breast nipple comprises implanting a prosthesis that includes a body formed of implantable biocompatible material and a base formed of implantable biocompatible material that is located at a first end of the body. The body has a shape to reconstruct the breast nipple and the base has a diameter that is larger than the body. Each of the body and the base has at least one opening extending therethrough.

In another embodiment, an implantable prosthesis comprises an implantable body having a shape to reconstruct the anatomical feature. The body includes a plurality of layers of biocompatible material. The body also includes a channel extending in an axial direction through each of the layers and a plurality of openings in communication with and extending in a lateral direction from the channel.

In a further embodiment, an implantable prosthesis comprises an implantable body having a shape to reconstruct the anatomical feature. The body includes a plurality of layers of biocompatible material arranged in a stacked configuration with one or more spacers located between adjacent layers to space the adjacent layers apart from each other.

In another embodiment, an implantable prosthesis comprises an implantable body having a shape to reconstruct the anatomical feature. The body including a plurality of layers of biocompatible material arranged in a stacked configuration with each layer having at least one opening extending therethrough to allow passage of fluid through the body.

In a further embodiment, a method of reconstructing an anatomical feature comprises implanting a prosthesis that includes a body having a shape to reconstruct the anatomical feature. The body includes a plurality of layers of biocompatible material arranged in a stacked configuration with one or more spacers located between adjacent layers to space the adjacent layers apart from each other.

BRIEF DESCRIPTION OF DRAWINGS

FIGS. 8-10 are exploded views of alternate prosthetic nipples employing stacks of layers having various opening configurations that may form random patterns of openings in the prosthesis;

FIGS. 11-13 are plan views taken along lines 11-11, 12-12 and 13-13 of FIGS. 8-10, respectively, illustrating overlap of random patterns of openings;

DETAILED DESCRIPTION

Figure 1:
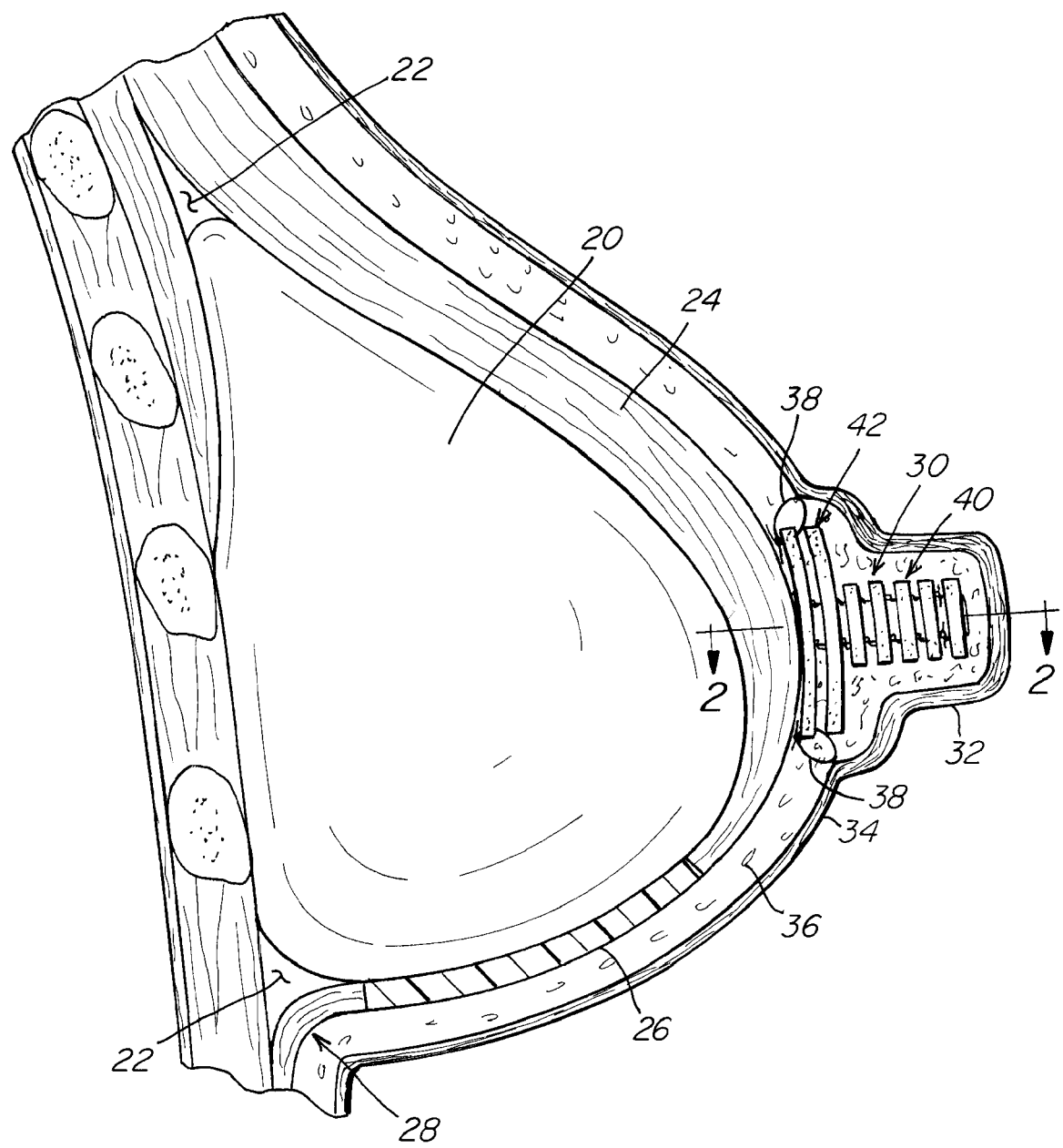
FIG. 1 is a schematic cross-sectional view of a breast reconstruction that employs a prosthetic nipple according to one embodiment of the invention.

An implantable prosthesis is provided for reconstructing or replacing an anatomical feature. The prosthesis may be configured to provide an amount of support and/or compliance sufficient to provide a look, feel and/or movement that may mimic or simulate the natural anatomical feature.

The prosthesis may be configured to allow tissue ingrowth, revascularization and/or neovascularization for reconstructing the anatomical feature. The prosthesis may be configured to allow fluid flow or passage therethrough to reduce seroma formation. The prosthesis may be formed from a biocompatible material that may integrate into surrounding tissue.

The prosthesis may include a body with a shape that mimics the anatomical feature. The prosthesis may also include a base that is located at an end of the body to facilitate anchoring the prosthesis in position.

The prosthesis may include stacked layers of biocompatible material. If desired, one or more layers of material may be removed or added to adjust the shape, including the height, of the prosthesis for a particular application.

A layer may be positioned in spaced relation to an adjacent layer. A spaced layer arrangement may provide the prosthesis with one or more openings between the layers that allow one or more of the following: fluid flow therethrough, tissue ingrowth, revascularization, neovascularization, and fat and/or stem cell deposition. The spaced layer arrangement may provide a desired tactile response and/or natural movement for the prosthesis.

The layers may be arranged to maintain a spacing therebetween so that the layers do not collapse upon each other. One or more spacers may be located between adjacent layers. Such an arrangement may help reduce the potential of the prosthesis collapsing into a relatively rigid mass of material after implantation.

The layers may be secured together using one or more lengths of suture or suture-like material. The layer spacing may be maintained by forming one or more knots in the suture between adjacent layers. The particular spacing between adjacent layers may be established by the size and/or number of knots formed in the suture between the layers. It is to be understood that other arrangements for spacing apart and maintaining adjacent layers in spaced relation may be employed as should be apparent to one of skill in the art.

For some applications, it may be desirable to construct the prosthesis with one or more channels or passages that allow fluid flow through the prosthesis to reduce the potential of seroma formation. The channel may be a continuous passage that extends partially or completely through a portion of the prosthesis, or the channel may be formed by one or more openings that extend through individual layers and together create the channel or passage when stacked together. The channel may have any suitable configuration as should be apparent to one of skill in the art. For example, and without limitation, the channel may extend in an end-to-end direction, and may be straight, angled, curved or multi-directional.

Each layer may have at least one opening extending therethrough. The openings may form a channel or passage to allow passage of fluid through the prosthesis to reduce the potential for seroma formation. The openings may also or alternatively facilitate tissue ingrowth, revascularization and/or neovascularization through the prosthesis. The openings may also or alternatively provide the prosthesis with a desired amount of support, compliance and/or feel. The openings may also or alternatively provide one or more spaces or voids in the prosthesis for receiving fat and/or stem cells to facilitate revascularization and/or tissue ingrowth. The openings may have any suitable configuration to provide the prosthesis with one or more of these or other desired characteristics as should be apparent to one of skill in the art.

For example, and without limitation, the openings may be circular, oval, rectangular, triangular, elongated, angled, curved or linear.

Each layer may include a uniform pattern of openings that may be aligned when assembled in the stacked configuration. Alternatively, two or more layers may include non-uniform or random patterns and/or sizes of openings. When stacked and assembled, the different openings and patterns may form a prosthesis having a random or non-uniform network of openings extending through the device that do not completely align with each other. Such an arrangement may be desirable for trapping and retaining fat and/or stem cells within the body of the prosthesis. The randomness of the openings may be desirable to enhance tissue ingrowth, revascularization and/or neovascularization to the prosthesis.

The body may have a cylindrical, conical or frusto-conical shape. For example, and without limitation, the layers may have a circular shape to provide the body with an overall shape that may mimic a nipple. The layers may be the same size to provide the body with a generally cylindrical configuration. Alternatively, one or more of the layers may have different sizes to provide the body with a generally conical or frusto-conical configuration. In this manner, the body may be formed so as to have a configuration that mimics or simulates the particular shape of a patient's natural nipple.

For some applications, the body may include a sidewall that extends from the base and an end wall located at an end of the sidewall opposite the base. The sidewall and the end wall may define a cavity within the body. The base and/or end wall may have an opening in communication with the cavity.

For some applications, it may be desirable to provide the body with additional support. The body may include a support structure that is located within the cavity. The support structure may extend from the base to an end wall. The support structure may be configured to provide a desired amount of compliance or resilience to the body.

The prosthesis may be formed from a biocompatible material that may integrate into surrounding tissue. The prosthesis may be formed from a biologic and/or synthetic material. The biologic material may or may not be cross-linked to provide the prosthesis with any desired amount of strength, flexibility and/or absorbability for one or more particular applications. For some applications, the prosthesis may include biologic materials having varying degrees of crosslinking to vary the strength, flexibility, absorbability and/or other property of one or more select portions of the prosthesis. For example, and without limitation, the prosthesis may be formed with material having more crosslinking toward the base and less crosslinking away from the base so that the flexibility of the prosthesis increases in a direction away from the base. For some applications, the prosthesis may include a combination of biologic and synthetic materials.

For ease of understanding, embodiments of the implantable prosthesis will be described below in connection with a prosthetic nipple for breast reconstruction. However, it is to be understood that aspects of the invention may be employed for a prosthesis having any shape suitable for reconstructing other anatomical features as should be apparent to one of skill in the art. For example, other applications for the prosthesis may include, but are not limited to, facial features such as a chin, a cheek or a nose.

In one illustrative embodiment shown in FIG. 1, a breast reconstruction may involve implanting a breast implant 20 within a pocket 22 that has been formed under the pectoralis major muscle 24. A sheet of biologic material 26 may be added to bridge a gap between the pectoralis major 24 and the inframammary fold 28.

For some breast reconstruction procedures, it may be desirable to reconstruct or replace the nipple. As shown in FIG. 1, a prosthetic nipple 30 may be implanted between the pectoralis major 24 and the nipple skin 32 to fill the natural diameter and volume of the nipple shape that may remain from the skin following a nipple sparing procedure in which the natural tissue and contents of the nipple have been removed during the surgical procedure. An end of the prosthesis may be supported against the pectoralis major and secured in position relative to the nipple skin.

During some procedures, the nipple skin with areola may be removed during a mastectomy. The prosthetic nipple may be implanted below a portion of skin in the anatomically correct position. The skin may be tattooed to mimic the natural shading of an areola and nipple as should be apparent to one of skill in the art.

In one embodiment, the prosthesis 30 may be secured to the skin 34 and/or underlying tissue 36 so that the prosthesis may drop or move freely with the reconstructed breast. If desired, the prosthesis may be secured to the pectoralis major muscle. The prosthesis 30 may be secured using one or more sutures 38. However, the prosthesis may be secured to muscle, tissue and/or skin, as desired, using any suitable technique as should be apparent to one of skill in the art.

In one embodiment, the prosthetic nipple 30 may be configured to maintain its shape, or return to its shape, when subjected to various external forces. The prosthesis may be configured to allow flow through of fluid for reducing the potential incidence of seroma formation. The prosthesis may be configured to permit tissue ingrowth, revascularization and/or neovascularization.

Figure 2:
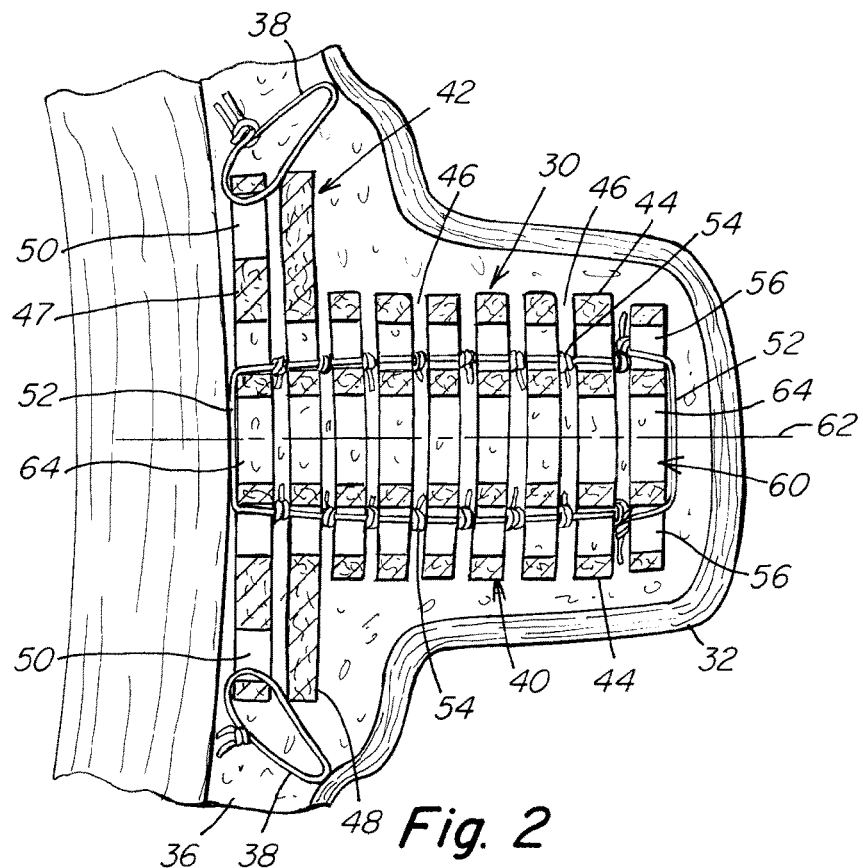
FIG. 2 is a cross-sectional view of the prosthetic nipple of FIG. 1 taken along section line 2-2.

In one illustrative embodiment as shown in FIGS. 1-2, the prosthesis 30 may include a body 40 with a shape that reconstructs or mimics a nipple. As shown, the body 40 may have a generally cylindrical shape, although other shapes are contemplated. The prosthetic nipple 30 may also include a base 42 that is located at one end of the body. In one embodiment, the base 42 may be configured to reconstruct or mimic a breast areola and, accordingly, is larger than the body. In this regard, the base may be configured with a size and/or structure for location in the region of the areola and to provide a degree of tactile response similar to an areola.

For some applications, it may be desirable for the prosthesis to permit one or more of the following functionalities: fluid flow, tissue ingrowth, revascularization and/or neovascularization for reconstructing the nipple.

In one illustrative embodiment shown in FIGS. 1-2, the body 40 may include a plurality of layers 44 of biocompatible material arranged in a stacked configuration. As shown, each layer 44 may be positioned in spaced relation to an adjacent layer to provide the prosthesis with channels or openings 46 between the layers for fluid flow, tissue ingrowth, revascularization and/or neovascularization. If desired, the channels or openings 46 may also be used for fat and/or stem cell deposition for supporting and/or providing a desired tactile response and/or natural movement for the prosthesis.

The base 42 may include one or more layers of biocompatible material located at an end of the body. The number and particular configuration of the base layers may depend on the particular characteristics desired for the base.

In one illustrative embodiment shown in FIGS. 1-2, the base 42 may include two layers of material. A first base layer 47 may act as an anchoring layer for the prosthesis. A second base layer 48 may provide additional structural support for the base. The base layers 47, 48 may be stacked one atop the other, as shown. The base layers 47, 48 may be spaced relative to each other and/or the body layers 44 to permit fluid flow, tissue ingrowth, revascularization and/or neovascularization. Spacing between the base layers also facilitates access to the first base layer 47 for anchoring the prosthesis with one or more fasteners.

In one embodiment, the first base layer 47 may include one or more holes 50 for securing the base with a fastener, such as a suture. The anchor holes 50 may be located in the outer or peripheral portion of the first layer 47 that extends beyond the body 40 to facilitate securement of the base 42. The peripheral holes 50 may also permit tissue ingrowth to the base over time to more permanently anchor the prosthesis in position. As shown, the base 42 may provide a relatively large surface area for securing and/or anchoring the prosthesis.

In one embodiment, the second base layer 48 may be free of peripheral holes to provide a more rigid layer as compared to the first base layer. Such an arrangement may provide a base that simulates the feel and tactile response of an areola. However, it is to be understood that each embodiment of the invention does not require a second layer for the base and that the second base layer, if provided, may employ any suitable configuration for providing any desired characteristics as should be apparent to one of skill in the art.

Figure 3:
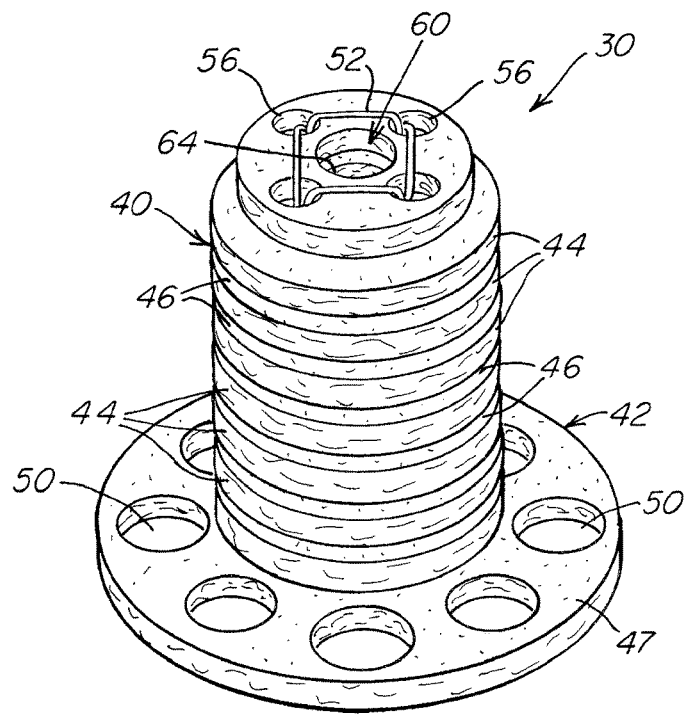
FIG. 3 is a perspective view of a prosthetic nipple according to another embodiment of the invention.

In one illustrative embodiment shown in FIG. 3, the base 42 may include a single layer 47 of biocompatible material that is located at an end of the body 40. As shown, the layer 47 may be provided with peripheral holes 50 for securing the base and the prosthesis with one or more fasteners. It is to be appreciated that the base may include any number of layers and each layer may have any configuration suitable for a particular application as should be apparent to one of skill in the art.

The layers, including the body layers 44 and the base layers 47, 48, may be arranged to maintain a spacing therebetween and maintain the shape of the prosthesis. Such an arrangement may help reduce the potential of the layers collapsing upon each other and transforming the prosthesis into a relatively rigid mass of material after implantation.

In one illustrative embodiment shown in FIGS. 1-2, the layers 44, 47, 48 may be secured together using one or more lengths of suture 52 or suture-like material. The suture may be absorbable or non-absorbable as should be apparent to one of skill in the art.

As illustrated in FIG. 2, the spacing between adjacent layers may be maintained by forming one or more knots 54 in the suture between each of the layers. The particular spacing between adjacent layers may be established by the number and/or size of knots formed between the layers. It is to be understood that other arrangements for spacing apart and maintaining adjacent layers in spaced relation may be employed as should be apparent to one of skill in the art. For example, and without limitation, one or more spacers may be integrally formed in a layer. Alternatively, one or more standoffs may be provided between adjacent layers.

In one embodiment, the spacing between each layer of the stack may be uniform. For example, the layers 44, 47, 48 may be uniformly spaced by providing similar knots 54 between adjacent layers. In another embodiment, the spacing may be varied between some or all of the layers. For example, and without limitation, the size and/or number of knots 54 between some layers may be smaller or larger than the size and/or number of knots between other layers.

One illustrative embodiment of a method of fabricating or assembling a prosthesis with a stacked configuration is described in connection with FIGS. 2 and 4-5.

Figure 4:
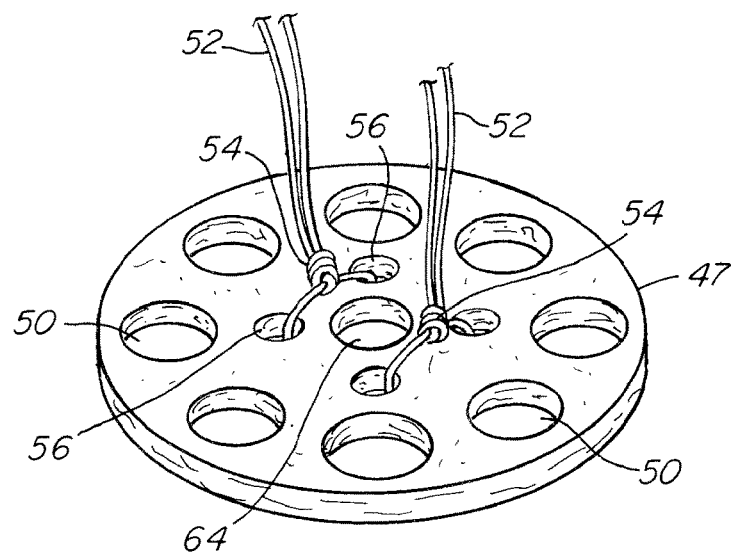
FIG. 4 is a perspective view of one embodiment of a base layer illustrating one method of fabricating the prosthetic nipples of FIGS. 1 and 3.

As shown in FIG. 4, several lengths of suture 52 may be extended or threaded through holes or openings 56 provided in the base layer 47 of the prosthesis. Each suture 52 is tied to form one or more knots 54 to create a desired amount of spacing between the next layer of material. Once knotted, the lengths of suture 52 are then threaded through another layer of material and again knotted. Additional layers may be added and secured in a similar manner until the desired number of layers are stacked and secured to form the prosthesis, such as shown in FIGS. 2 and 3.

Figure 5:
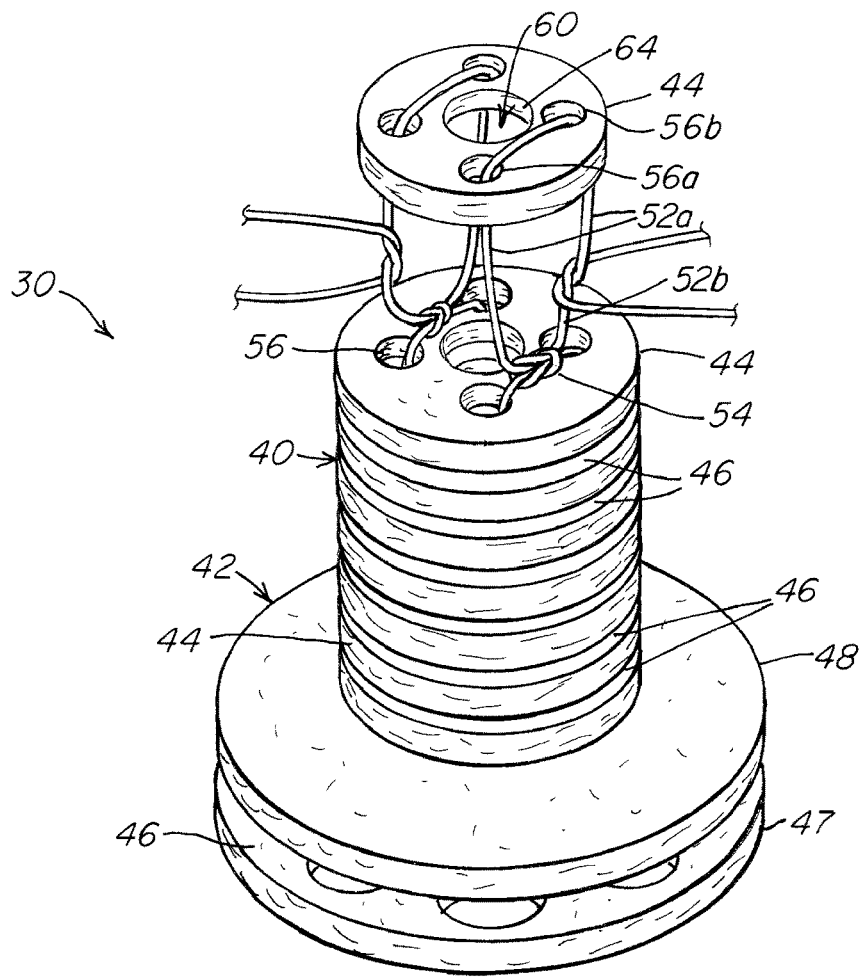
FIG. 5 is a partially exploded perspective view of the prosthetic nipple of FIGS. 1-2 illustrating assembly of the outermost layer of the body.

As shown in FIG. 5, the outermost or final layer 44 of the body 40 may be secured to the stack by threading a first end 52a of a suture 52 up through one hole 56a in the outer layer and back down through another hole 56b in the layer. The first end 52a of the suture is then tied off with a second end 52b of the suture with the last knot being hidden between the outermost layer and its adjacent layer. Other sutures securing the stack of layers may be tied off in a similar manner.

As described above, assembly of the prosthesis may be initiated with the anchor layer 47 of the base 42 and built up toward the outermost layer 44 of the body 40. However, it is to be appreciated that the prosthesis may be assembled in the reverse manner from the outermost body layer 44 to the anchor layer 47 of the base, if desired.

For some applications, it may be desirable to construct the prosthesis with one or more channels or passages that allow fluid flow through the prosthesis to reduce the potential of seroma formation. The channel may be a continuous passage that extends through a portion of the prosthesis, or the channel may be formed by one or more openings that extend through individual layers and together create the channel or passage when stacked together.

In one illustrative embodiment shown in FIGS. 1-5, the prosthesis may include a channel 60 or passage that extends along part or the entire length of the body 40 and the base 42. As shown, the channel 60 may be centrally located along the longitudinal axis 62 of the prosthesis. The channel 60 may be formed by at least one opening 64 extending through each layer 44, 47, 48 of the prosthesis which align when the layers are stacked and secured together to form the prosthesis.

For some applications, the channel may be offset from the longitudinal axis and/or located in other regions of the prosthesis. If desired, the channel may be angled relative to the longitudinal axis, curved and/or extend in multiple directions to provide a desired pathway through the prosthesis.

The longitudinal channel 60 may communicate with one or more transverse or lateral channels or openings 46 located between adjacent layers to allow fluid flow through the prosthesis in both the axial and lateral directions. The channel may also permit tissue ingrowth, revascularization and/or neovascularization to the prosthesis.

As illustrated in FIGS. 1-5, each layer 44, 47, 48 may also include holes or openings 56 for securing the layers together with a suture, as described above. If desired, these openings 56 may be configured to form additional channels or passages through the prosthesis for fluid flow, tissue ingrowth, revascularization and/or neovascularization.

The number, configuration and pattern of the holes or openings 56 may be selected to provide any desired characteristics as should be apparent to one of skill in the art. For example, in addition to fluid flow, tissue ingrowth and/or vascularization characteristics, the compliance or resiliency of the prosthesis may be changed by varying the number, size, shape and/or pattern of holes or openings provided in one or more of the layers of material.

In the illustrative embodiments of FIGS. 1-5, some or all of the layers 44, 47, 48 of the prosthesis may include a first hole or opening 64 that is centrally located to form a channel 60 along the longitudinal axis 62 of the prosthesis. Some or all of the layers may also include a group of second holes 56 arranged in a generally square or diamond pattern that includes four holes. As described above, the second holes 56 may be used for securing the layers together with suture. The second holes 56 may also form additional channels or passages through the prosthesis.

Figure 6:
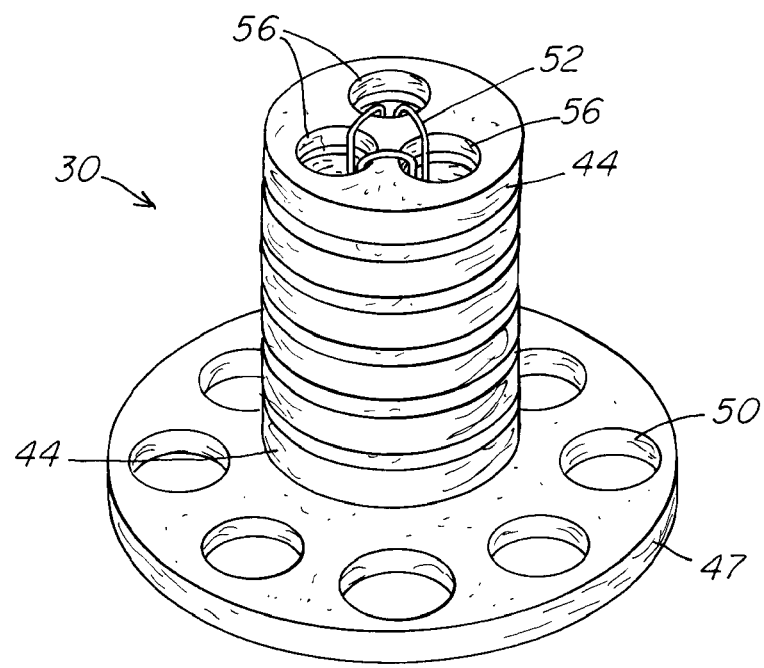
FIG. 6 is a perspective view of a prosthetic nipple according to another embodiment of the invention.

In one illustrative embodiment shown in FIG. 6, each layer 44, 47 may include three holes or openings 56 arranged in a triangular pattern. In one illustrative embodiment shown in FIG. 7, each layer 44, 47, 48 may include a pair of holes or openings 56 located on opposite side of the longitudinal axis 62. As shown, the holes 56 may be used for securing the layers together with suture. The holes 56 may also create channels or passages that extend along part or the entire length of the prosthesis. The channels may communicate with the lateral channels or openings created between adjacent layers to allow fluid flow, tissue ingrowth and/or vascularization through the prosthesis in the axial and lateral directions.

In the embodiments described above, each of the layers may employ a uniform pattern of holes or openings 56, 64 that align with each other when the layers are assembled in the stacked configuration. The anchor layer 47 of the base may have additional peripheral holes 50 for securing the prosthesis in position during the reconstruction procedure. However, it is to be understood that two or more of the layers may include holes or openings having different sizes, shapes and/or patterns.

FIGS. 8-10 illustrate several examples of layers of material with holes or openings that may have different sizes, shapes and patterns on two or more of the layers. A prosthetic nipple may be formed by assembling the layers in a manner described above.

FIG. 8 illustrates a plurality of layers 44, 47, 48 for a prosthesis that may include circular holes 56, 64 having different sizes with a different number of holes that are arranged in different patterns on two or more of the layers.

FIG. 9 illustrates a plurality of layers 44, 47, 48 for a prosthesis that may include circular holes 56 having the same size with a different number of holes that are arranged in different patterns on two or more of the layers.

FIG. 10 illustrates a plurality of layers 44, 47, 48 for a prosthesis that may include circular holes 56 and elongated slots 66 or other openings having the same size with a different number of holes that are arranged in different patterns on two or more of the layers.

When stacked and assembled, the different openings and patterns may form a prosthesis having a random or non-uniform network of openings extending through the device that do not completely align with each other. Such an arrangement may be desirable for trapping and retaining fat and stem cells within the body of the prosthesis. The randomness of the openings may be desirable to enhance tissue ingrowth, revascularization and/or neovascularization to the prosthesis.

FIGS. 11-13 illustrate examples of non-aligned or random openings that may extend through a prosthesis when using layers having non-uniform opening sizes, shapes and patterns, such as the layers illustrated in FIGS. 8-10.

Figure 7:
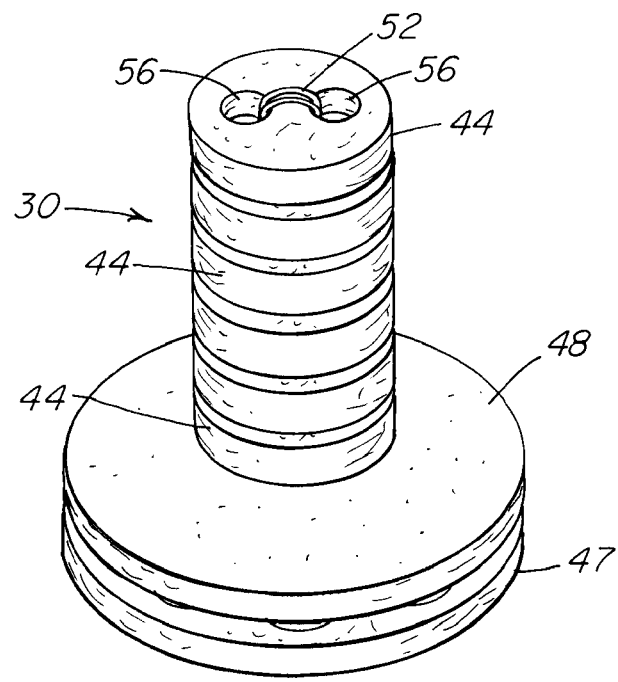
FIG. 7 is a perspective view of a prosthetic nipple according to another embodiment of the invention.

The body 40 and the base 42 of the prosthesis may employ any shape suitable for a particular application. As illustrated in the embodiments of FIGS. 1-7, the prosthesis 30 may include a body 40 having a generally cylindrical shape with a size suitable for reconstructing a nipple. As illustrated in FIGS. 3 and 6-7, the nipple body 40 may have a larger (FIG. 3) to smaller (FIG. 7) outer dimension, such as diameter. The length of the body may be increased or decreased by adding or removing layers. In this regard, the length of the body may be decreased by severing the suture between one or more of the layers that are to be removed from the body. This arrangement allows a surgeon to quickly adjust the length of the nipple body during a reconstruction procedure.

The prosthesis may include a base 42 having a circular shape with a diameter that is larger than the body 40 and suitable for reconstructing the areola. The thickness of the base may be varied by employing two or more layers 47, 48 (FIGS. 2, 5 and 7) or a single layer 47 (FIGS. 3 and 6).

Figure 14:
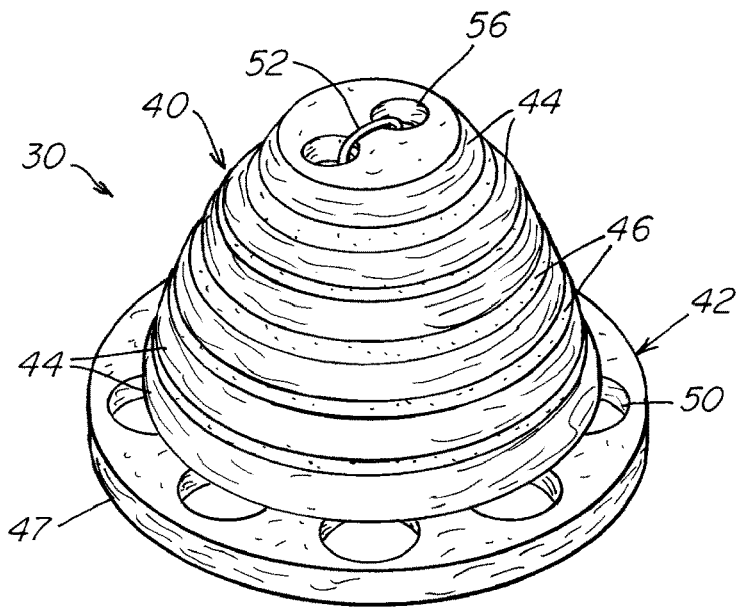
FIG. 14 is a perspective view of a prosthetic nipple with a body having a frusto-conical shape according to another embodiment of the invention.

In one illustrative embodiment shown in FIG. 14, the prosthetic nipple 30 may include a body 40 having a frusto-conical shape that may be suitable for reconstructing a natural nipple having a similar shape. The body 40 may be formed with layers 44 of material having outer dimensions, such as diameters, that decrease in a direction from the base 42 toward the outermost layer of material.

In one illustrative embodiment, a prosthesis may be formed with stacked layers having a thickness of approximately 0.040 inches (1 mm) that are spaced apart to form a gap or opening of approximately 0.020 to 0.030 inches (0.5 to 0.75 mm). Each layer may have one or more holes or openings having a diameter of approximately 0.062 to 0.125 inches (1.5 to 3 mm). Each body layer may have a diameter of approximately 0.25 to 0.50 inches (6 to 12 mm) and each base layer may have a diameter of approximately 0.75 to 1.0 inches (19 to 25 mm). The body 40 may have a height of approximately 0.50 to 0.75 inches (12 to 19 mm). It is to be understood that the prosthesis may configured with features having any suitable size and/or shape as should apparent to one of skill for any particular application.

The various embodiments described above employ a stacked layer arrangement for the prosthesis. However, it is to be understood that the prosthesis may employ other structural arrangements of materials to provide the prosthesis with any suitable combination of desired features and/or characteristics.

Figure 15:
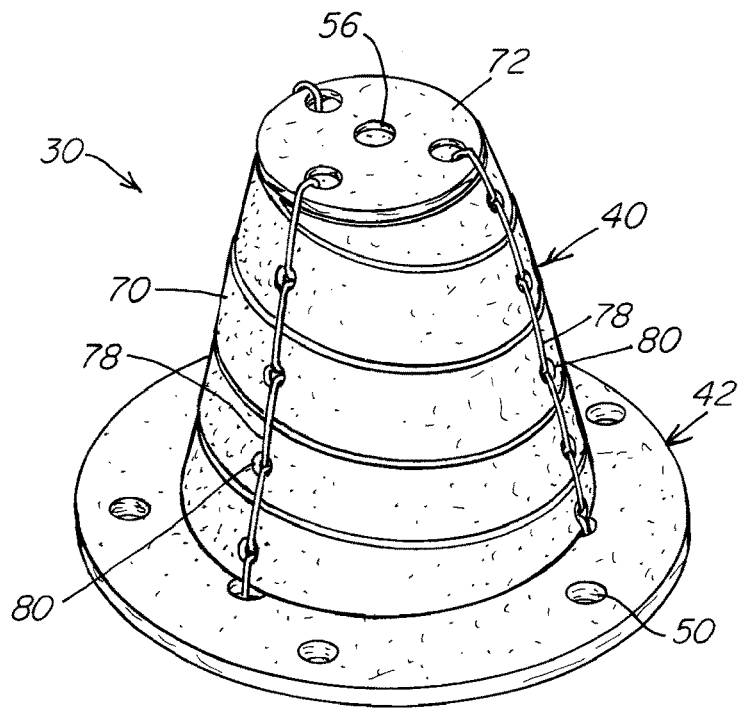
FIG. 15 is a perspective view of a prosthetic nipple according to another embodiment of the invention.
Figure 16:
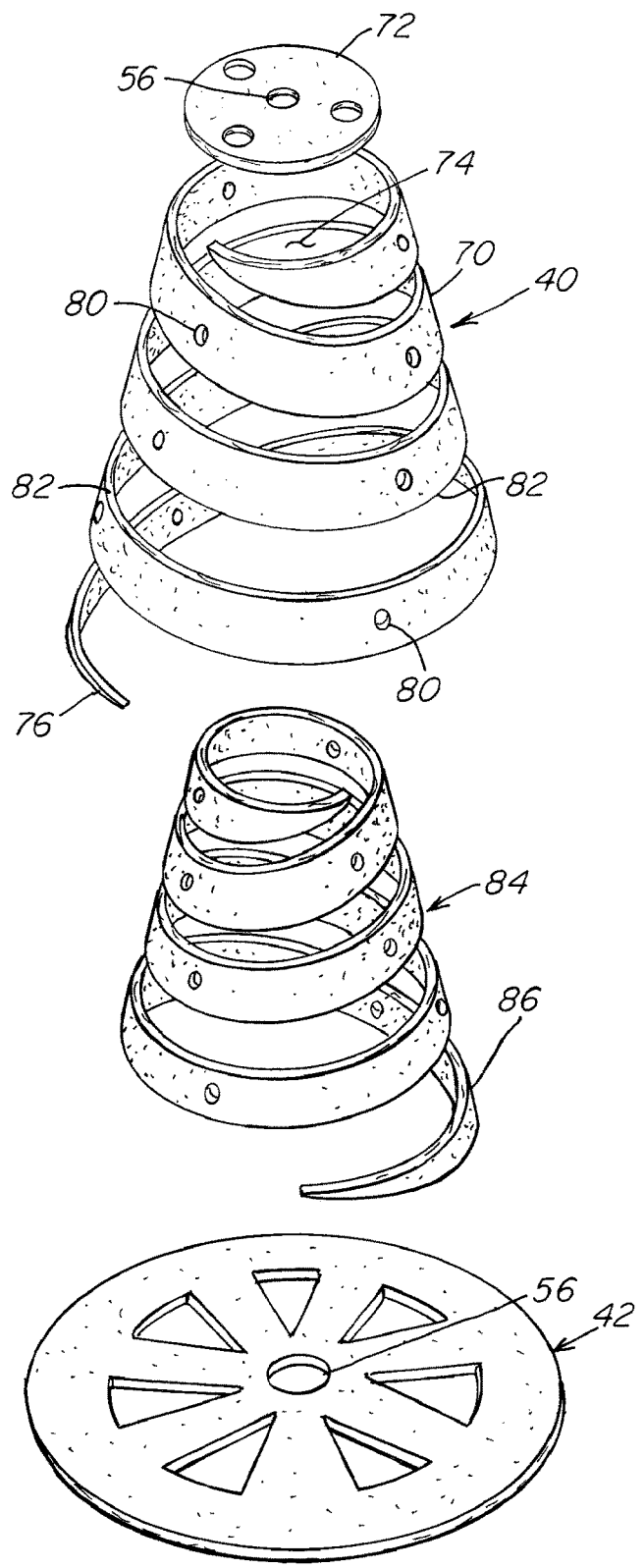
FIG. 16 is an exploded perspective view of the prosthetic nipple of FIG. 15.

In one illustrative embodiment shown in FIGS. 15-16, the prosthetic nipple 30 may include a body 40 having a shape to reconstruct a breast nipple and a base 42 located at a first end of the body with a diameter that is larger than the body. The body 40 may include a sidewall 70 that extends from the base 42 and an end wall 72 located at an end of the sidewall opposite the base 42. The sidewall 70 and the end wall 72 define a cavity 74 within the body.

The body 40 has a relatively hollow configuration that may provide greater radial compression to external radial forces and less axial compression to external axial forces as compared to the stacked configurations described above. The body may have a cavity 74 that may be particularly suitable for receiving fat and/or stem cell deposits or injections.

The base 42 and the end wall 72 may each have at least one opening or hole 56 in communication with the cavity. Such an arrangement may allow fluid flow, tissue ingrowth, revascularization and/or neovascularization through the prosthesis. The holes 56 may also provide access to the internal cavity 74 for injecting fat and/or stem cells, if desired.

As illustrated, the body 40 may have a frusto-conical shape to mimic a breast nipple. However, the body may be configured to have any shape suitable for reconstructing a nipple as should be apparent to one of skill in the art. For example, and without limitation, other body shapes may include conical, cylindrical or hourglass shapes.

In one illustrative embodiment, the body may be formed from a length or strip 76 of biocompatible material that is wrapped into the desired shape. In one embodiment, the sidewall 70 may be formed by wrapping the material in a helix or spiral pattern. However, it is to be understood that the sidewall 70 may be formed by wrapping the material in any suitable pattern as should be apparent to one of skill in the art.

The body material may be retained in the desired shape using one or more fasteners. In one embodiment, the sidewall 70 may be formed by securing or retaining the material in the desired shape with one or more lengths of suture 78 or suture-like material. As illustrated, the suture 78 may extend in a vertical direction and be anchored in holes 80 that are aligned when the material is placed in the desired shape. One or more knots may be formed in the suture and located on the inner side of the material to retain the suture in the hole. It is to be understood that any suitable fastener or fastening scheme may be used to retain the body material in the desired shape. For example, and without limitation, the edges of the wrapped material may be adhered or bonded together using a suitable adhesive for the particular material as should be apparent to one of skill.

In one embodiment, the material may be wrapped to position adjacent edges 82 of the wrapped material in close proximity to each other so that there is a minimal, if any, gap between the edges. However, the sidewall 70 may be configured with adjacent edges 82 of material being spaced apart to form an opening therebetween that may allow fluid flow, tissue ingrowth, revascularization and/or neovascularization through the sidewall of the body.

The base 42 and the end wall 72 may be secured to the opposing ends of the body using one or more fasteners. In one embodiment, the base 42 and end wall 72 may be secured to the body sidewall using the sutures 78 that also retain the sidewall material in the desired shape. If desired, separate fasteners may be used to secure the base and end wall to the sidewall.

For some applications, it may be desirable to provide the body with additional support or structure to vary the compliance and/or tissue ingrowth characteristics of the prosthesis. In one illustrative embodiment shown in FIG. 16, the prosthesis may include an inner body or support structure 84 that is located within the cavity 74 of the body 40. The inner body may be configured to extend from the base 42 to the end wall 72. The inner body may be configured to provide a desired amount of structural support and/or reduce the amount of space within the cavity 74 to facilitate tissue ingrowth, revascularization and/or neovascularization through the prosthesis.

As illustrated, the inner body 84 may have a tapered or conical shape similar to the outer body 40. However, the inner body may be configured to have any shape suitable for providing support to the outer body as should be apparent to one of skill in the art.

In one illustrative embodiment, the inner body 84 may be formed from a length or strip 86 of biocompatible material that is wrapped into the desired shape. In one embodiment, the inner body 84 may be formed by wrapping the material in a helix or spiral pattern. As illustrated, the inner body may employ a spiral pattern that is wrapped in a direction opposite to the body sidewall 70. However, it is to be understood that the inner body may be formed by wrapping the material in any suitable pattern as should be apparent to one of skill in the art.

The inner body 84 may be retained in the desired shape using one or more fasteners in a manner similar to the body, as described above. If desired, the inner body may be attached to the base and/or end wall using the fasteners, such as sutures, that also retain the inner body material in the desired shape, although separate fasteners may be used to secure the base and end wall to the inner body. It is to be understood that any suitable fastener or fastening scheme may be used to retain the inner body material in the desired shape and/or attach the inner body to the base or end wall as should be apparent to one of skill.

As indicated above, the prosthesis may be configured with various structural arrangements of materials to provide the prosthesis with any suitable combination of desired features and/or characteristics.

Figure 17:
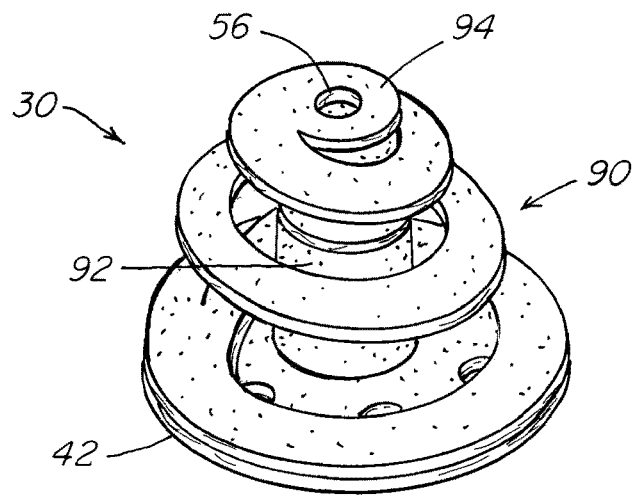
FIG. 17 is a perspective view of a prosthetic nipple according to another embodiment of the invention.
Figure 18:
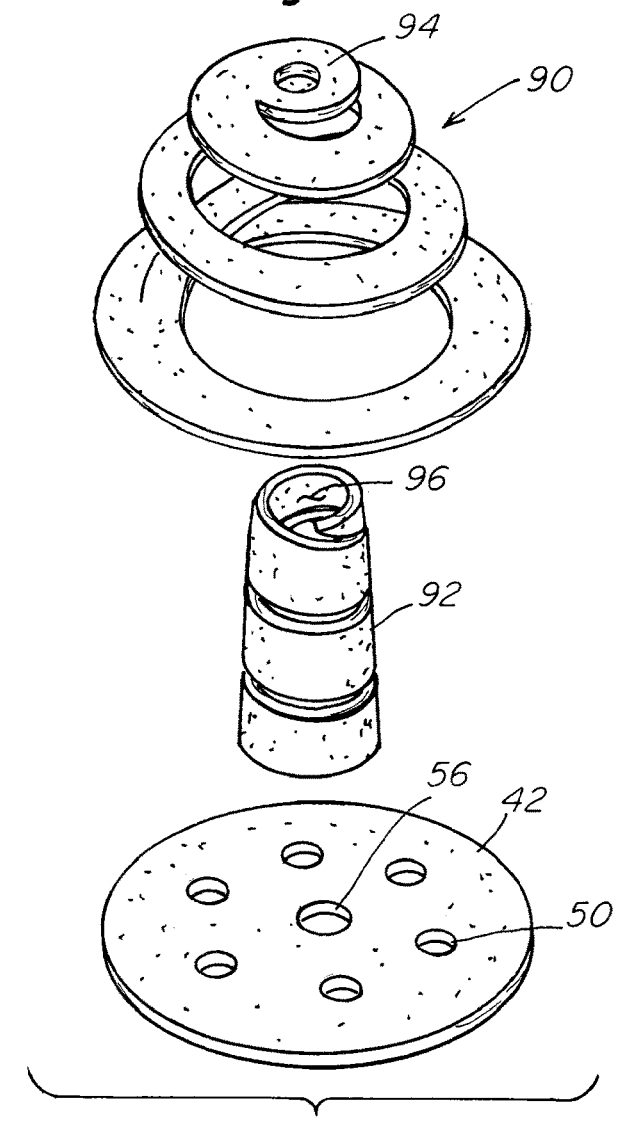
FIG. 18 is an exploded perspective view of the prosthetic nipple of FIG. 17.

In one illustrative embodiment shown in FIGS. 17-18, the prosthetic nipple 30 may include an outer body 90 having a flat coil configuration and an inner body or support 92 that maintains the outer body at a desired height. As shown, the inner body 92 may extend between a base 42 and a central region 94 of the outer body that forms an end wall for the prosthesis. The inner body 92 may be configured with a cavity 96 that may be suitable for receiving fat and/or stem cell deposits or injections.

The base 42 and the central region or end wall 94 may each have at least one opening or hole 56 in communication with the cavity. Such an arrangement may allow fluid flow, tissue ingrowth, revascularization and/or neovascularization through the prosthesis. The holes 56 may also provide access to the internal cavity 96 for injecting fat and/or stem cells, if desired.

As illustrated, the outer body 90 may have a generally tapered or conical shape to mimic a breast nipple. The coiled winding may produce a relatively soft outer body that allows fat cells to be squeezed around the body and provide a soft tactile response. However, the outer body may be configured to have any shape suitable for reconstructing a nipple as should be apparent to one of skill in the art.

In one illustrative embodiment, the outer body 90 may be formed from a sheet of biocompatible material that is sliced, cut or punched with a helix or spiral pattern. A central region of the material may be lifted away from the sheet to form a raised coiled configuration, as shown. However, it is to be understood that the outer body may be formed using any suitable pattern as should be apparent to one of skill in the art.

As illustrated, the inner body 92 may have a tapered or conical shape. However, the inner body may be configured to have any shape suitable for providing support to the outer body as should be apparent to one of skill in the art.

In one embodiment, the inner body 92 may be formed from a length or strip of biocompatible material that is wrapped in a helix or spiral pattern. However, it is to be understood that the inner body may be formed by wrapping the material in any suitable pattern to produce any desired shape as should be apparent to one of skill in the art.

The inner body 92 may be retained in the desired shape using one or more fasteners, such as sutures, or adhesive. If desired, the inner body may be attached to the base and/or end wall using fasteners, such as sutures, or adhesive. It is to be understood that any suitable fastener or fastening scheme may be used to retain the inner body material in the desired shape and/or attach the inner body to the base or end wall as should be apparent to one of skill.

The prosthesis may employ any biocompatible material suitable for a particular application as should be apparent to one of skill in the art.

In one embodiment, the prosthesis may be formed from a biologic that may be cross-linked, partially cross-linked or not cross-linked to provide a desired amount of strength, flexibility and/or longevity suitable for the application. The origin of the biologic material may be porcine, bovine or human. Examples of a biologic material that may be suitable for the prosthesis include, but are not limited to, ALLOMAX and COLLAMEND, which are both available from C.R. Bard, Inc. The prosthesis may be hydrated, if desired, prior to implantation.

In other embodiments, the prosthesis may be formed of a synthetic material or a combination of biologic and synthetic materials to provide the prosthesis with desirable properties and/or characteristics as should be apparent to one of skill in the art.

For certain applications or reconstructive procedures, it may be desirable to provide the prosthesis with one or more components for facilitating or enhancing the procedure.

In one embodiment, the prosthetic material may be coated with one or more antibiotic components. Illustrative examples of antibiotic components include, but are not limited to, minocycline hydrochloride and rifampin. The antibiotic components may be spray coated onto the materials using an L-tyrosine polymer. However, it to be understood that any suitable antibiotic, if desired, may be integrated with the prosthesis using other techniques as should be apparent to one of skill in the art.

In one embodiment, the prosthetic material may be coated or impregnated with one or more growth factors for a particular medical application. Any growth factors may be integrated with the prosthesis using any suitable techniques as should be apparent to one of skill in the art.

It should be understood that the foregoing description of various embodiments of the invention are intended merely to be illustrative thereof and that other embodiments, modifications, and equivalents of the invention are within the scope of the invention recited in the claims appended hereto.

What is claimed is:

1. An implantable prosthetic nipple comprising:
a nipple body formed of implantable biologic material, the body configured to reconstruct a breast nipple; and
a base formed of implantable biologic material that is located at a first end of the body, the base having a dimension that is larger than the body with an outer peripheral portion thereof extending in an outward radial direction beyond the body;
each of the body and the base having at least one opening extending therethrough in an axial direction, the outer peripheral portion of the base including a plurality of axial openings extending therethrough in the axial direction and positioned around the body, the body including a plurality of disks that are arranged in a stacked configuration, each disk having at least one opening extending therethrough that is configured to allow passage of fluid through the body.

2. The implantable prosthetic nipple according to claim 1, wherein the base is configured to reconstruct a breast areola.

3. The implantable prosthetic nipple according to claim 1, wherein the body is configured to support tissue ingrowth, revascularization and/or neovascularization.

4. The implantable prosthetic nipple according to claim 1, wherein the base is configured to support tissue ingrowth, revascularization and/or neovascularization.

5. The implantable prosthetic nipple according to claim 1, wherein two or more disks have a plurality of openings extending therethrough.

6. The implantable prosthetic nipple according to claim 5, wherein the disks include a uniform pattern of openings relative to each other.

7. The implantable prosthetic nipple according to claim 5, wherein at least two disks include non-uniform patterns of openings relative to each other.

8. The implantable prosthetic nipple according to claim 1, wherein each disk is positioned in spaced relation to an adjacent disk.

9. The implantable prosthetic nipple according to claim 8, wherein the disks are fixed in position to maintain the spaced relation.

10. The implantable prosthetic nipple according to claim 8, wherein adjacent disks are maintained in spaced relation by one or more spacers located between the adjacent disks.

11. The implantable prosthetic nipple according to claim 1, wherein the body has a cylindrical shape.

12. The implantable prosthetic nipple according to claim 1, wherein the body has a frusto-conical shape.

13. The implantable prosthetic nipple according to claim 1, wherein the biologic material is absorbable.

14. An implantable prosthetic nipple comprising:
a nipple body formed of implantable biologic material, the body configured to reconstruct a breast nipple; and
a base formed of implantable biologic material that is located at a first end of the body, the base having a dimension that is larger than the body with an outer peripheral portion thereof extending in an outward radial direction beyond the body;
each of the body and the base having at least one opening extending therethrough in an axial direction, the outer peripheral portion of the base including a plurality of axial openings extending therethrough in the axial direction and positioned around the body;
the body including a channel extending therethrough in the axial direction and a plurality of lateral openings in communication with and extending in a lateral direction from the channel.

15. An implantable prosthetic nipple comprising:
a nipple body formed of implantable biologic material, the body configured to reconstruct a breast nipple; and
a base formed of implantable biologic material that is located at a first end of the body, the base having a dimension that is larger than the body with an outer peripheral portion thereof extending in an outward radial direction beyond the body;
each of the body and the base having at least one opening extending therethrough in an axial direction, the outer peripheral portion of the base including a plurality of axial openings extending therethrough in the axial direction and positioned around the body,
wherein the body includes a sidewall that extends from the base and an end wall located at an end of the sidewall opposite the base, the body including a cavity located between the base and the end wall, the base having at least one opening in communication with the cavity, the sidewall being formed from a length of material arranged in a helical or spiral configuration.

16. The implantable prosthetic nipple according to claim 15, wherein the end wall has at least one opening in communication with the cavity.

17. The implantable prosthetic nipple according to claim 15, further comprising a support located within the cavity to support the body.

18. An implantable prosthetic nipple comprising:
a nipple body formed of implantable biologic material, the body configured to reconstruct a breast nipple;
a base formed of implantable biologic material that is located at a first end of the body, the base having a dimension that is larger than the body with an outer peripheral portion thereof extending in an outward radial direction beyond the body;
wherein each of the body and the base has at least one opening extending therethrough in an axial direction, the outer peripheral portion of the base including a plurality of axial openings extending therethrough in the axial direction and positioned around the body;
wherein the body includes a sidewall that extends from the base and an end wall located at an end of the sidewall opposite the base, the body including a cavity located between the base and the end wall, the base having at least one opening in communication with the cavity; and
a support located within the cavity to support the body, the support having a helical or spiral configuration.

19. The implantable prosthetic nipple according to claim 18, wherein the support extends from the base to the end wall.

20. An implantable prosthetic nipple comprising:
a base formed of an implantable biologic material and configured to reconstruct a breast areola; and
a nipple body formed of an implantable biologic material supported by the base, the body configured to reconstruct a breast nipple and including a plurality of disks that are arranged in a stacked configuration with each disk being spaced apart from an adjacent disk, each of the body and the base configured to support tissue ingrowth, revascularization and/or neovascularization, the body including a channel extending in an axial direction through each of the disks and a plurality of openings in communication with and extending in a lateral direction from the channel.

21. The implantable prosthetic nipple according to claim 20, wherein each disk has at least one opening extending therethrough that is configured to allow passage of fluid through the body.

22. The implantable prosthetic nipple according to claim 21, wherein two or more disks have a plurality of openings extending therethrough.

23. The implantable prosthetic nipple according to claim 22, wherein the disks include a uniform pattern of openings relative to each other.

24. The implantable prosthetic nipple according to claim 22, wherein at least two disks include non-uniform patterns of openings relative to each other.

25. The implantable prosthetic nipple according to claim 20, wherein the disks are fixed in position to maintain adjacent disks in a spaced apart relation.

26. The implantable prosthetic nipple according to claim 20, wherein adjacent disks are maintained in a spaced apart relation by one or more spacers located between the adjacent disks.

27. The implantable prosthetic nipple according to claim 20, wherein the disks are secured together with one or more sutures.

28. The implantable prosthetic nipple according to claim 27, wherein adjacent disks are maintained in a spaced apart relation by one or more spacers located between the adjacent disks, the spacers including one or more knots that are formed in the suture.

29. The implantable prosthetic nipple according to claim 20, wherein the body has a cylindrical shape.

30. The implantable prosthetic nipple according to claim 20, wherein the body has a frusto-conical shape.

31. The implantable prosthetic nipple according to claim 20, wherein the biologic material is absorbable.

32. The implantable prosthetic nipple according to claim 20, wherein the base includes an outer peripheral portion extending in an outward radial direction beyond the body, the outer peripheral portion including a plurality of openings extending therethrough.

* * * * *